(12) United States Patent
Nakamura

(10) Patent No.: US 8,784,748 B2
(45) Date of Patent: Jul. 22, 2014

(54) DRY TEST STRIP FOR MEASURING CALCIUM

(75) Inventor: Tsutomu Nakamura, Kyoto (JP)

(73) Assignee: Arkray, Inc., Kyoto (JP)

( * ) Notice: Subject to any disclaimer, the term of this patent is extended or adjusted under 35 U.S.C. 154(b) by 76 days.

(21) Appl. No.: 13/457,291

(22) Filed: Apr. 26, 2012

(65) Prior Publication Data

US 2012/0275969 A1 Nov. 1, 2012

(30) Foreign Application Priority Data

Apr. 28, 2011 (JP) ................................. 2011-102424

(51) Int. Cl.
*G01N 33/52* (2006.01)
*G01N 33/84* (2006.01)

(52) U.S. Cl.
CPC ............ *G01N 33/526* (2013.01); *G01N 33/523* (2013.01); *G01N 33/84* (2013.01)
USPC .............. 422/421; 422/426; 436/79; 436/170

(58) Field of Classification Search
USPC .............................. 422/421, 426; 436/79, 170
See application file for complete search history.

(56) References Cited

U.S. PATENT DOCUMENTS 4,594,225 A * 6/1986 Arai et al. ...................... 422/423
5,709,837 A * 1/1998 Mori et al. ..................... 422/423

FOREIGN PATENT DOCUMENTS

| EP | 0254202 A1 | 1/1988 |
| JP | 05-232108 A | 9/1993 |
| WO | WO 96/04554 A1 | 2/1996 |

OTHER PUBLICATIONS

European Search Report Re corresponding Application No. 12165791,0 dated Nov. 26, 2012,.
Knoll, H. et al., The Determination of Calcium Glucose, Urea and Uric Acid Using the Kodak Ektachem Multilayer Film Technology: An Evaluation, Journal of Clinical Chemistry and Clinical Biochemistry, vol. 20, No. 7, 1982, pp. 491-498.

* cited by examiner

*Primary Examiner* — Jill Warden
(74) *Attorney, Agent, or Firm* — Knobbe Martens Olson & Bear LLP

(57) ABSTRACT

A dry test strip for measuring calcium is comprising a support, a reagent layer provided on the support, and a reagent holding layer provided on the reagent layer, and containing, as reagents, o-cresolphthalene complexone, a magnesium selective masking agent, and a pH buffer for adjusting the pH of the environment for reaction of the o-cresolphthalene complexone with calcium to 10.0-11.0, wherein such reagents are present in either the reagent layer or the reagent holding layer or the both layers.

15 Claims, 5 Drawing Sheets

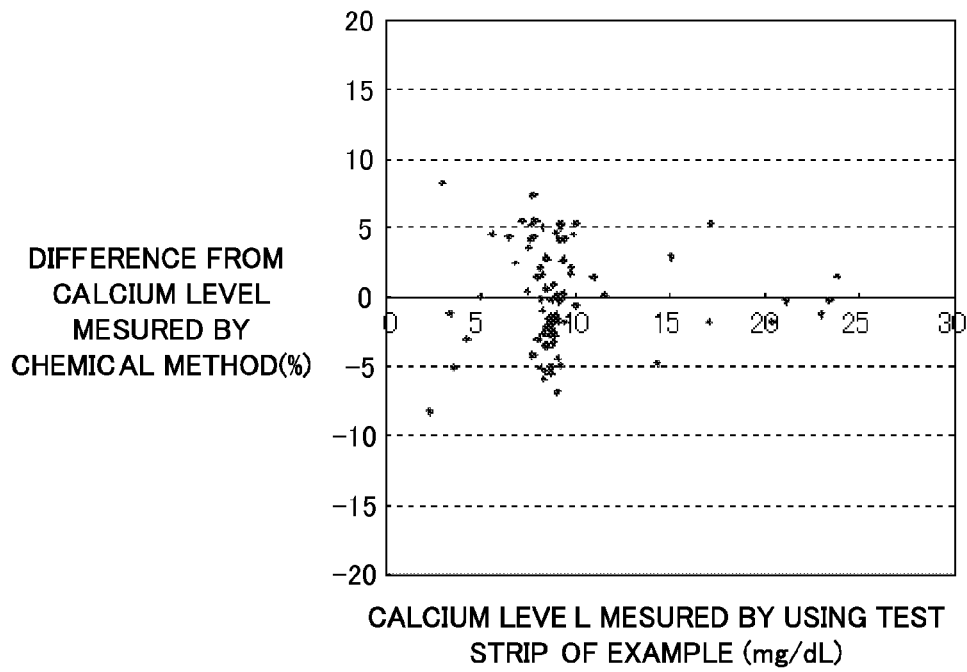
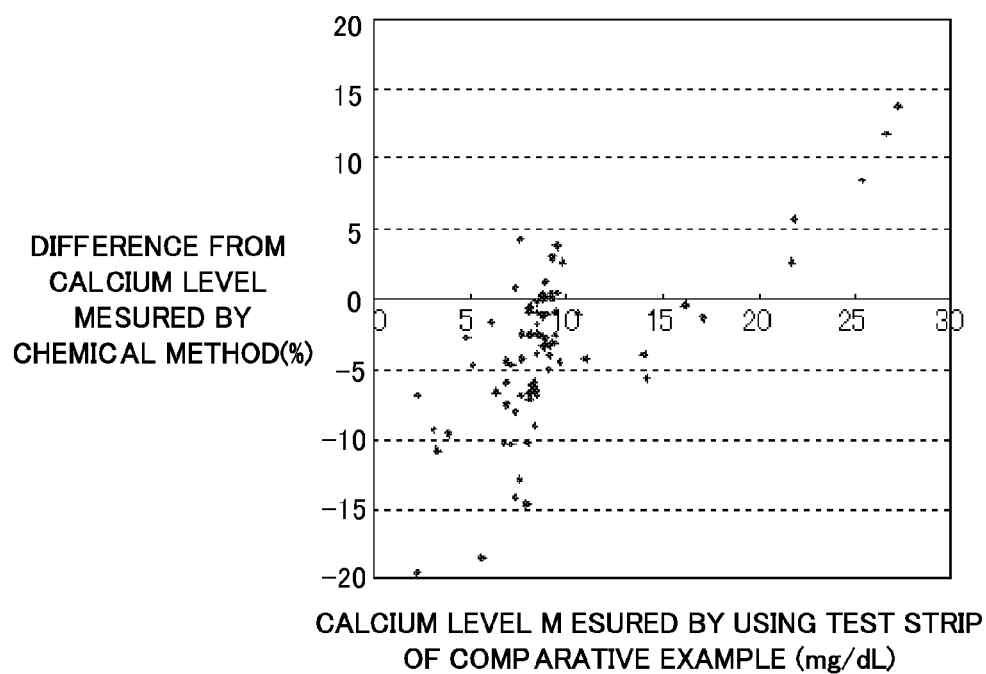

DRY TEST STRIP FOR MEASURING CALCIUM

CROSS-REFERENCE TO RELATED APPLICATION

This application is based on Japanese Patent Application No. 2011-102424 filed on Apr. 28, 2011. The description, claims, and drawings of Japanese Patent Application No. 2011-102424 are incorporated by reference herein.

FIELD

The present invention relates to a dry test strip for measuring calcium.

BACKGROUND

Calcium is one of the essential elements for a variety of animals including human, and is intimately involved in the various reactions occurring in vivo. Thus, a measurement of the level of calcium in serum or plasma is one of the important clinical laboratory parameters.

A dry test strip produced by applying to or impregnating in a support a reagent which reacts with calcium to generate color and then drying the support is commonly used in order to rapidly measure a blood calcium level in initial diagnosis such as mass medical examination and screening study.

Unexamined Japanese Patent Application KOKAI Publication No. H05-232108 discloses a dry test strip which comprises a support, a reagent layer formed on part of the support surface, a reagent holding layer which covers at least part of the reagent layer and at least part of the support. The reagent holding layer is formed by braiding synthetic fiber filaments. Thus, a liquid specimen spotted onto the reagent holding layer is absorbed and spread to contact with the reagent layer. If the liquid specimen contains a substance of interest, the substance reacts with the reagent contained in the reagent layer to generate color. A method for determining the presence of color generation or intensity of color visually or using an optical measurement means (colorimetric method) can be used to rapidly and conveniently detect or quantify a substance of interest.

Known colorimetric methods for measuring calcium include the OCPC method in which calcium is allowed to chelate with o-cresolphthalene complexone (OCPC) under alkaline conditions. A dry test strip for measuring calcium which the strip applies such OCPC method uses an alkaline buffer such as a boric acid buffer (pH 9.2).

SUMMARY

The dry test strip for measuring calcium by the OCPC method, however, has the problem of a large measurement error. And in such dry test strip for measuring calcium, a large measurement error occurs due to magnesium. Thus, for example, a hypermagnesemia specimen often exhibits a high calcium level due to magnesium. Also, a dry test strip has generally the problem that when the strip is stored for a long time, the reagent degrades because of its deliquescent nature and the like, which causes a large measurement error.

The present invention has been developed in view of the foregoing problems, and an object of the invention is to provide a dry test strip for measuring calcium with a smaller measurement error.

In order to achieve the object described above, a dry test strip for measuring calcium according to the aspect of the invention is comprising o-cresolphthalene complexone, a magnesium selective masking agent, and a pH buffer for adjusting the pH of the environment for reaction of the o-cresolphthalene complexone with calcium to 10.0-11.0.

The pH buffer is preferably at least one selected from the group consisting of N-cyclohexyl-3-aminopropanesulfonic acid, N-methyl-D-glucamine, and a carbonate buffer. A 9:1 mixture of N-cyclohexyl-3-aminopropanesulfonic acid and N-methyl-D-glucamine are especially preferred.

The magnesium selective masking agent is preferably 8-hydroxyquinoline.

Preferably, the dry test strip for measuring calcium further contains a surfactant. The surfactant is especially preferably p-t-octyl phenol polyoxyethylene.

Preferably, the dry test strip for measuring calcium is comprising
a support,
a reagent layer provided on the support, and
a reagent holding layer provided on the reagent layer,
wherein the o-cresolphthalene complexone, the magnesium selective masking agent, and the pH buffer are each contained in either the reagent layer or the reagent holding layer or the both layers.

BRIEF DESCRIPTION OF THE DRAWINGS

A more complete understanding of this application can be obtained when the following detailed description is considered in conjunction with the following drawings, in which:

FIG. 5A is a diagram which shows the difference of a calcium level measured by using a dry test strip of an example of the invention from a calcium level measured by an enzymatic method where the level measured by the enzymatic method is set to 100%; and FIG. 5B is a diagram which shows the difference of a calcium level measured by using a dry test strip of a comparative example of the invention from a calcium level measured by an enzymatic method where the level measured by the enzymatic method is set to 100%.

DETAILED DESCRIPTION

First Embodiment

Figure 1A:
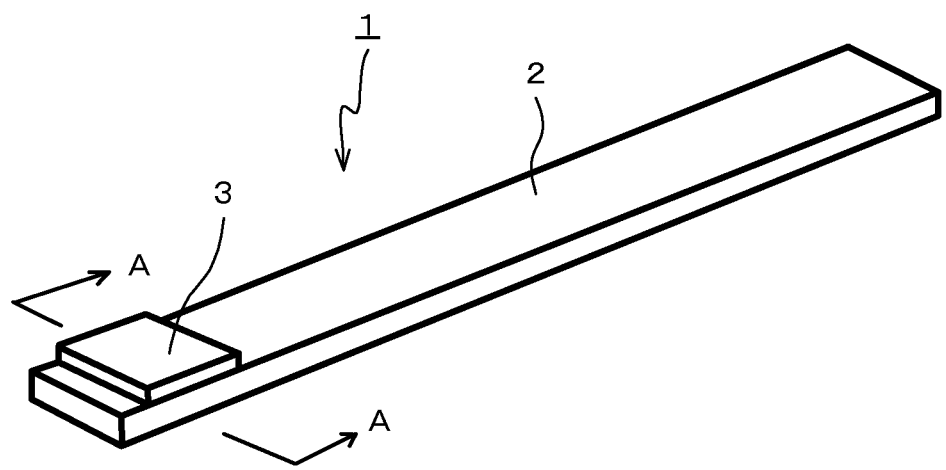
FIG. 1A is a perspective view which shows the structure of a dry test strip for measuring calcium according to the first embodiment of the invention.
Figure 1B:
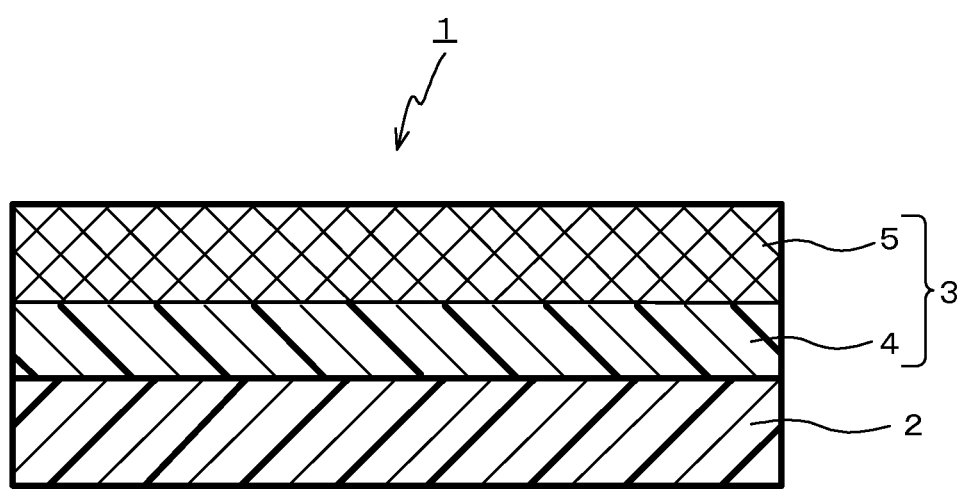
FIG. 1B is a cross sectional view taken along the line A-A in FIG. 1A.

As described in FIGS. 1A and 1B, dry test strip for measuring calcium 1 according to the first embodiment of the invention consists of support 2 and reagent portion 3 supported by support 2. Reagent portion 3 consists of reagent layer 4 formed on support 2 and reagent holding layer 5 configured to cover reagent layer 4.

Support 2 is preferably liquid impermeable, whereby a liquid specimen added dropwise onto reagent layer 4 and reagent holding layer 5 remains in reagent layer 4 and reagent holding layer 5 when dry test strip for measuring calcium 1 according to the first embodiment of the invention is used to measure calcium. Thus calcium can be precisely measured. A strip which can be used for support 2 includes a paper strip, a plastic (synthetic resin) strip, a metal strip, and the like. It is preferred to use the synthetic resin strip in terms of mass productivity, low costs, preservation, water resistance, and the like.

In the case in which after dropwise addition of a liquid specimen to cause the detection reaction, the dry test strip is irradiated from the support side for optical analysis, support 2 should be light transmissive. In contrast, in the case in which the dry test strip is irradiated from the side of reagent holding layer 5, support 2 does not have to be light transmissive.

Reagent layer 4 contains o-cresolphthalene complexone (OCPC) and a magnesium selective masking agent. The magnesium selective masking agent can be, for example, 8-hydroxyquinoline or the like.

Reagent layer 4 is mainly made of a liquid permeable material. Particularly, it is preferred that reagent layer 4 is mainly made of a water soluble material in which the reagents are dispersed. This allows the reagents contained in reagent layer 4 to be incorporated into the liquid specimen added dropwise onto reagent holding layer 5, which is located on reagent layer 4. The water soluble material which can be used includes water soluble polymer compounds such as polyvinylpyrrolidone (PVP), and the like. Reagent layer 4 may also be made of a liquid permeable fabric material such as a paper, knit, or woven material in which the reagents are dispersed.

Reagent holding layer 5 contains a pH buffer. The pH buffer is preferably a buffer which adjusts the pH of the environment for reaction of OCPC with calcium to the range of from 10.0 to 11.0, and of which components do not volatilize even when the layer is dried. The pH buffer more preferably has both a low deliquescent nature and a high solubility in terms of preservation. The pH buffer which can be used includes, for example, N-cyclohexyl-3-aminopropanesulfonic acid (CAPS), N-methyl-D-glucamine (MEG), a carbonate buffer, or the like. A 9:1 mixture of CAPS and MEG is especially preferred in terms of the deliquescent nature and solubility. Use of such buffer with both of a low deliquescent nature and a high solubility gives dry test strip for measuring calcium 1, which is less likely to increase a measurement error even after long storage.

Reagent holding layer 5 is mainly made of a liquid permeable material. Particularly, it is preferred that reagent holding layer 5 is mainly made of a water soluble material in which the reagent is dispersed. This allows the liquid specimen added dropwise onto reagent holding layer 5 to rapidly and uniformly spread within reagent holding layer 5. The water soluble material which can be used includes water soluble polymer compounds such as polyvinylpyrrolidone (PVP). Reagent holding layer 5 may also be made of a liquid permeable fabric material such as a paper, knit, or woven material in which the reagent is dispersed.

Reagent holding layer 5 may be directly formed on reagent layer 4. Alternatively, reagent holding layer 5 may be disposed on reagent layer 4 via a liquid permeable layer.

In the case in which the amount of a liquid specimen to be evaluated by using dry test strip for measuring calcium 1 is extremely small (for example, about 5 μl), reagent layer 4 and reagent holding layer 5 may have a length of several millimeters and a width of several millimeters. In this case, it is difficult to hold the layers by hand or the like. Thus, it is preferred to form support 2 as an elongated strip which has a width of from several millimeters to about 1 centimeter, so as to allow it to be used as a handle.

Dry test strip for measuring calcium 1 according to the first embodiment of the invention can be produced as follows.

First, a sheet which is made of a specified material for support 2 and which has a predetermined thickness is cut to provide an elongated strip which has a predetermined size. The elongated strip is washed and dried to give support 2.

Next, reagent layer 4 is produced. First, o-cresolphthalene complexone (OCPC) and a magnesium selective masking agent are dispersed in a liquid permeable material.

In the case in which the liquid permeable material is a water soluble material such as a water soluble polymer compound, first the material is dissolved in pure water to form an aqueous solution. Then the reagents described above are dissolved in the aqueous solution and stirred to disperse the reagents. Next, the resultant is applied to a predetermined area of support 2 and dried to form reagent layer 4.

In the case in which the liquid permeable material is a fabric material such as a paper, knit, or woven material, the aqueous solution which is formed by dissolving the reagents described above in pure water and stirring the resultant solution is absorbed and dispersed in the fabric material which has a predetermined size. And the resultant is dried to remove the water whereby giving reagent layer 4. Then reagent layer 4 is laminated onto support 2. In the case in which reagent layer 4 is mainly made of a water soluble material, the lamination is achieved by wetting the bottom surface of reagent layer 4 with pure water and press bonded to a predetermined area of support 2. This allows the water soluble material of the bottom surface to be dissolved and to act as an adhesive. Alternatively, reagent layer 4 may be bonded to support 2 with an adhesive.

Next, reagent holding layer 5 is produced. First, a pH buffer is dispersed in a liquid permeable material.

In the case in which the liquid permeable material is a water soluble material such as a water soluble polymer compound, the material is dissolved in pure water to form an aqueous solution. Then the pH buffer is dissolved in the aqueous solution and stirred to disperse the buffer. Next, the resultant is applied to a flat substrate and dried. Then the dried material is removed from the substrate to give reagent holding layer 5.

In the case in which the liquid permeable material is a fabric material such as a paper, knit, or woven material, the aqueous solution which is formed by dissolving the pH buffer in pure water and stirring the resultant solution is absorbed and dispersed in the fabric material which has a predetermined size. Then the resultant is dried to remove the water whereby giving reagent holding layer 5.

After reagent holding layer 5 is produced, reagent holding layer 5 is laminated onto reagent layer 4.

For example, reagent holding layer 5 may be laminated onto reagent layer 4 via an adhesive layer which is made of an adhesive (not shown). The adhesive layer should be liquid permeable. In the case in which the adhesive layer is formed by applying an adhesive to almost the entire surface of reagent layer 4, the adhesive is preferably liquid permeable. Or the adhesive may be applied so that the adhesive layer is liquid permeable, rather than applied to almost the entire surface of reagent layer 4.

As an alternative, in the case in which reagent holding layer 5 is mainly made of a water soluble material, the bottom surface of reagent holding layer 5 is wetted with pure water and press bonded to a predetermined area of reagent layer 4. This allows the water soluble material of the bottom surface to be dissolved and to act as an adhesive.

In this way, dry test strip for measuring calcium 1 according to the first embodiment of the invention can be produced.

Dry test strip for measuring calcium 1 according to the first embodiment of the invention can be used in the following manner to measure calcium.

A predetermined fixed amount of a liquid specimen (serum or plasma) is added dropwise onto reagent holding layer 5. The liquid specimen quickly spreads over reagent holding layer 5. Then the specimen is permeated into reagent layer 4 underlying reagent holding layer 5 to combine all of the reagents, whereby forming a reaction liquid which has a pH of from 10.0 to 11.0. In the alkaline reaction liquid, the OCPC forms a complex with the calcium in the liquid specimen. Generally, calcium, which is bound to protein such as albumin, has poor reactivity with OCPC. But in the dry test strip according to the first embodiment of the invention, because the reaction liquid has a high pH of from 10.0 to 11.0, the OCPC reacts with calcium, which is bound to such protein, to form a complex.

Although the OCPC can form a complex with the magnesium in the liquid specimen, the dry test strip contains the masking agent which chelates with magnesium more intensely than OCPC, and thus the OCPC is prevented from forming a complex with the magnesium. Especially, in the case in which 8-hydroxyquinoline is used as the masking agent, the 8-hydroxyquinoline binds to the magnesium in a more specific manner in the reaction environment at a pH of from 10.0 to 11.0, relative to the conventional reaction environment at a pH of 9.2. Thus the strip can be expected to provide a better masking effect.

In this way, calcium can be selectively detected. Because the absorption peak of the complex of OCPC and calcium is at about 570 nm, reagent layer 4 takes on a red-purple color.

After the completion of the reaction, the degree of the color generated (K/S value) is determined by applying visible light to reagent holding layer 5 and receiving the reflected light. The K/S value indicates the degree of color generation, and the value is determined by utilizing the fact that a higher degree of color generation (color density) provides a higher intensity of the reflected light. In other words, when R is the reflectance of the visible light, the K/S value is calculated by the following formula:

$$K/S = (1-R)^2/2R \quad \text{(Formula)}$$

An optical analyzer which applies such analytical method includes, for example, Fuji DRI-CHEM® 7000 from Fujifilm Corporation, CHOLESTECH LDX® KM from KONICA MINOLTA HOLDINGS, INC., SPOTCHEM® EZ from Arkray, Inc., and the like.

The K/S value obtained in this way can be used to determine the precise level of the calcium in a liquid specimen.

Second Embodiment

Figure 2A:
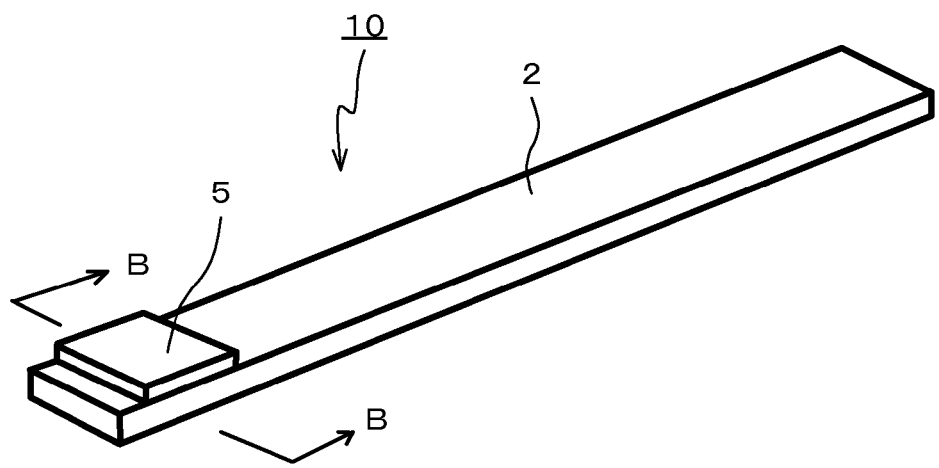
FIG. 2A is a perspective view which shows the structure of a dry test strip for measuring calcium according to the second embodiment of the invention.
Figure 2B:
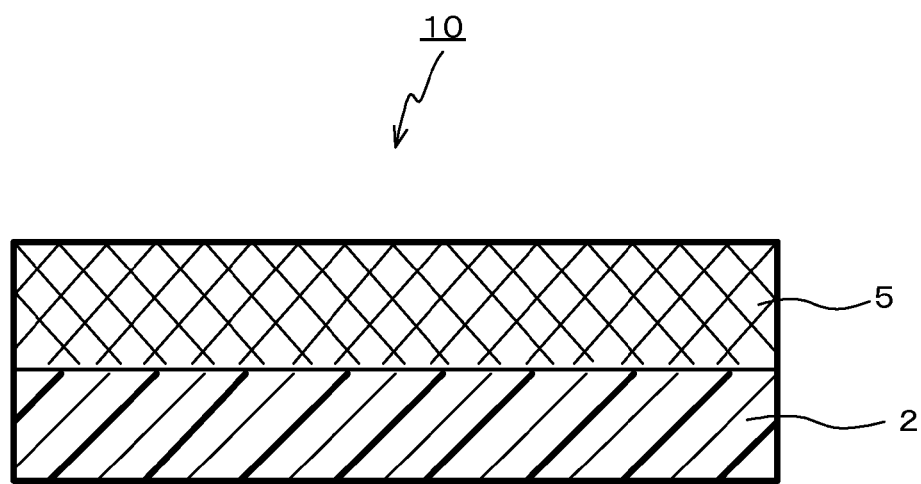
FIG. 2B is a cross sectional view taken along the line B-B in FIG. 2A.

In a dry test strip for measuring calcium according to the first embodiment, reagent layer 4 contains o-cresolphthalene complexone (OCPC) and a magnesium selective masking agent, while reagent holding layer 5 contains a pH buffer. But these reagents may be contained in any of reagent layer 4 or reagent holding layer 5. This is because whether the reagents are contained in reagent layer 4 or reagent holding layer 5, the reagents are combined in the reaction liquid formed after a liquid specimen is added dropwise. In the case in which the reagents are contained in only one of reagent layer 4 and reagent holding layer 5, the layer which does not contain the reagents can be omitted. If reagent layer 4 is omitted, reagent holding layer 5 is disposed on support 2. FIGS. 2A and 2B show dry test strip for measuring calcium 10 in the case in which reagent layer 4 is omitted. In dry test strip for measuring calcium 10 according to the second embodiment, reagent holding layer 5 may be disposed on support 2 via adhesive layer 6. Alternatively, reagent holding layer 5 may be directly formed on support 2 by application or the like.

Third Embodiment

In a dry test strip for measuring calcium according to the third embodiment, reagent layer 4 or reagent holding layer 5 further contains surfactant in addition to the reagents as in the first embodiment.

When a common metal chelate reaction system including OCPC is used to measure the level of calcium in serum or plasma, it is known that protein, especially albumin, in the specimen has an influence. In serum or plasma of normal persons, the percentage of calcium which adsorbs to albumin is fairly constant (about 40%), and thus the influence can be avoided by adding an appropriate numerical offset when measuring calcium. Thus practically, a dry test strip according to the first embodiment generally causes no problems. However, when measuring a rare specimen which has an unusually high level of albumin, the influence of the albumin may not be avoided if a simple numerical offset is added.

In the dry test strip for measuring calcium according to the third embodiment, the surfactant contained in reagent layer 4 or reagent holding layer 5 solubilizes the protein contained in a specimen when measuring calcium. Because the solubilized albumin has a decreased ability to bind to calcium, such strip can measure the calcium level of a specimen which has an unusually high level of albumin, without influence by adsorption of the calcium to the albumin. The specific examples of nonionic surfactants include p-t-octyl phenol polyoxyethylene (Triton X-45, Triton X-100, Triton X-114, Triton X-305, and the like). The specific examples of ionic surfactants include anion surfactants such as sodium dodecyl sulfate, and cationic surfactants such as tetradecyltrimethylammonium bromide. One skilled in the art will appreciate, however, that any compounds which are a surfactant with similar action may be used.

Example

Hereinafter, the invention will be explained in more detail with reference to examples, although the invention is not limited thereto. Unless otherwise specified, deionized water was used as pure water.

First, a white polyethylene terephthalate (PET) sheet which had a thickness of 0.2 mm was cut to provide an elongated strip which had a length of 70 mm and a width of 5 mm, and the strip was used as the support.

Next, a buffer which was a mixture of N-cyclohexyl-3-aminopropanesulfonic acid (CAPS) (from Dojindo Laboratories) and N-methyl-D-glucamine (MEG) (from Wako Pure Chemical Industries) was prepared. The mixed buffer is formed by dissolving 0.89 g of CAPS and 3.12 g of MEG in distilled water; adding a 4N—NaOH solution to the resultant to adjust the pH at 37° C. to 10.5; and filling the resultant up to 25 ml.

Next, 36 mg of o-cresolphthalene complexone (from Dojindo Laboratories) and 0.36 g of 8-hydroxyquinoline (from Wako Pure Chemical Industries) were dissolved in 4 ml of the mixed buffer prepared by the above method. After the solution was stirred well and defoamed by centrifugation, the overall amount of the solution was applied to one end of the support to have a length of 7 mm, a width of 5 mm, and a thickness of 0.15 mm. Then the applied solution was dried at 40° C. for 20 minutes to completely evaporate the water, whereby forming a film like reagent layer.

A reagent holding layer which was mainly made of a fabric material was laminated onto the reagent layer. As the fabric material, SAVINA® from KB Seiren was used. 0.1 g of Triton X-305 (from Wako Pure Chemical Industries) was dissolved in 10 ml of pure water. After the aqueous solution was stirred well and defoamed by centrifugation, the overall amount of the solution was impregnated into SAVINA® which had a length of 7 mm, a width of 5 mm, and a thickness of 0.2 mm. Then the fabric was dried at 40° C. for 20 minutes to completely evaporate the water.

The resultant reagent holding layer was laminated onto the reagent layer by using an acrylic adhesive.

Comparative Example

For a comparative example, a sodium borate buffer (pH 9.2) (from Wako Pure Chemical Industries) was used in place of the mixed buffer of CAPS/MEG to form a reagent layer. Except for this, a dry test strip was produced in the same manner as in the example described above.

(Measurement Operation)

SPOTCHEM® EZ desktop reflectometer from Arkray was used as the measurement device. A dry test strip for measuring calcium was placed on the table which was conditioned at a temperature of 37° C., and then 5.0 µl of a specimen was spotted onto the strip. After 3 minutes, the reflectance (R) at a wavelength of 575 nm was measured. The reflectance (R) was converted to a K/S value by using the Kubelka-Munk formula $(K/S=(1-R)^2/2R)$. A specimen which had a known calcium level was measured to predetermine a calibration curve between the K/S value and the calcium level. Based on the curve, the level of calcium in a specimen was calculated.

(Comparison of Influence of Magnesium)

Figure 3:
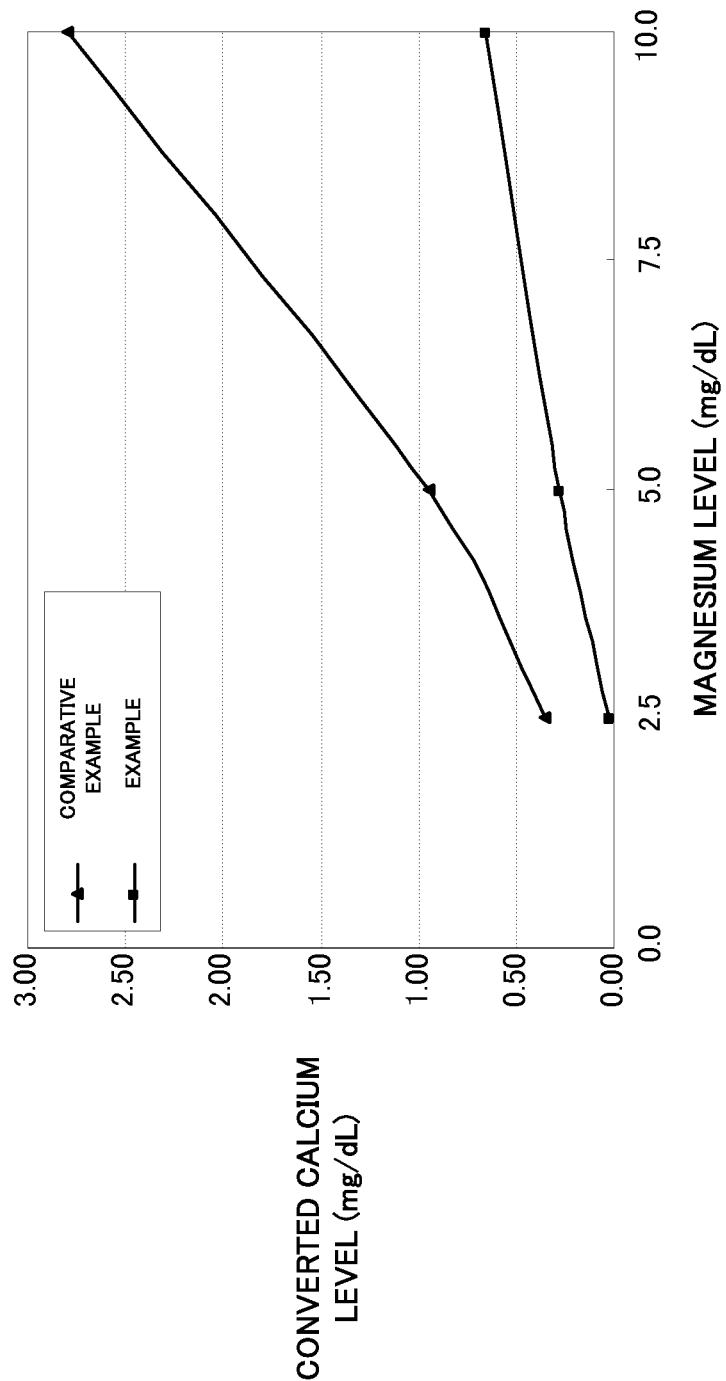
FIG. 3 is a diagram which shows the influence of magnesium on a dry test strip for measuring calcium of an example of the invention.

To compare the influence of magnesium on the dry test strips for measuring calcium, a specimen of an aqueous magnesium chloride solution which had a magnesium level of 2.5-10.0 mg/dL was spotted onto each of the dry test strips of the example and the comparative example, and the resultant strips were measured by the measurement device in the manner described above. FIG. 3 shows a plot of the degree of reaction (color generation) of the dry test strips for measuring calcium with the magnesium as calcium levels. A normal person has a serum magnesium level of about 2.5 mg/dL. At the magnesium level, the dry test strip for measuring calcium of the example showed little nonspecific reaction. And at a magnesium level of up to 10.0 mg/dL, the dry test strip of the example showed a nonspecific reaction of only about 0.50 mg/dL in calcium level terms. This is about 5% of the serum calcium level of a normal person, which is 8.4-10.2 mg/dL, and thus it is sufficiently low.

(Correlation Test)

Figure 4A:
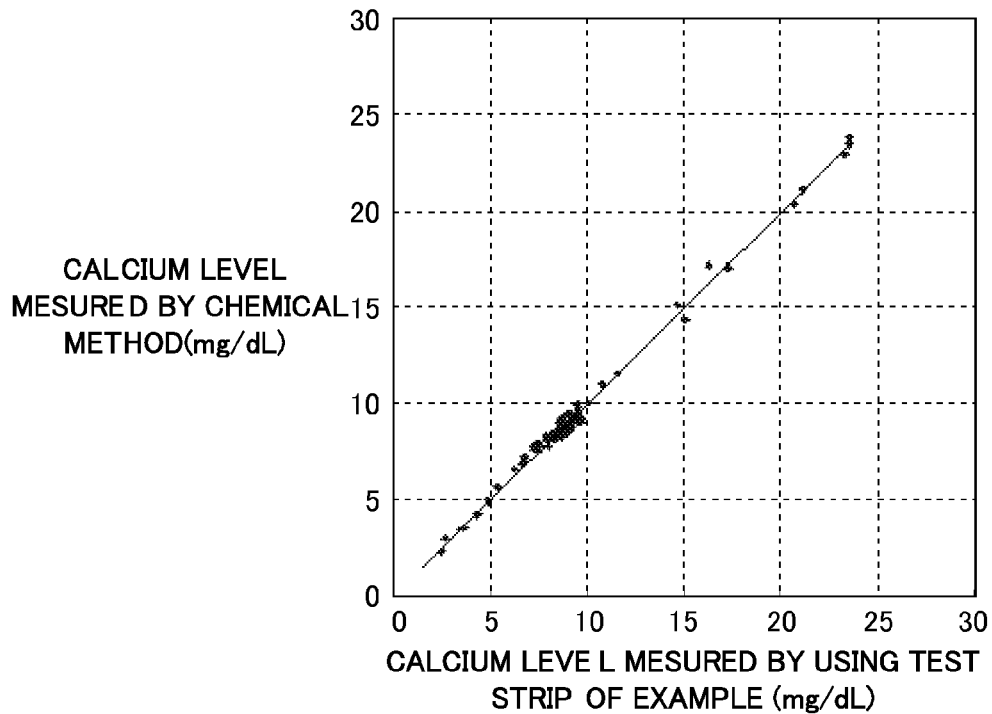
FIG. 4A is a plot of the calcium levels measured by using a dry test strip for measuring calcium of an example of the invention against the calcium levels measured by an enzymatic method.
Figure 4B:
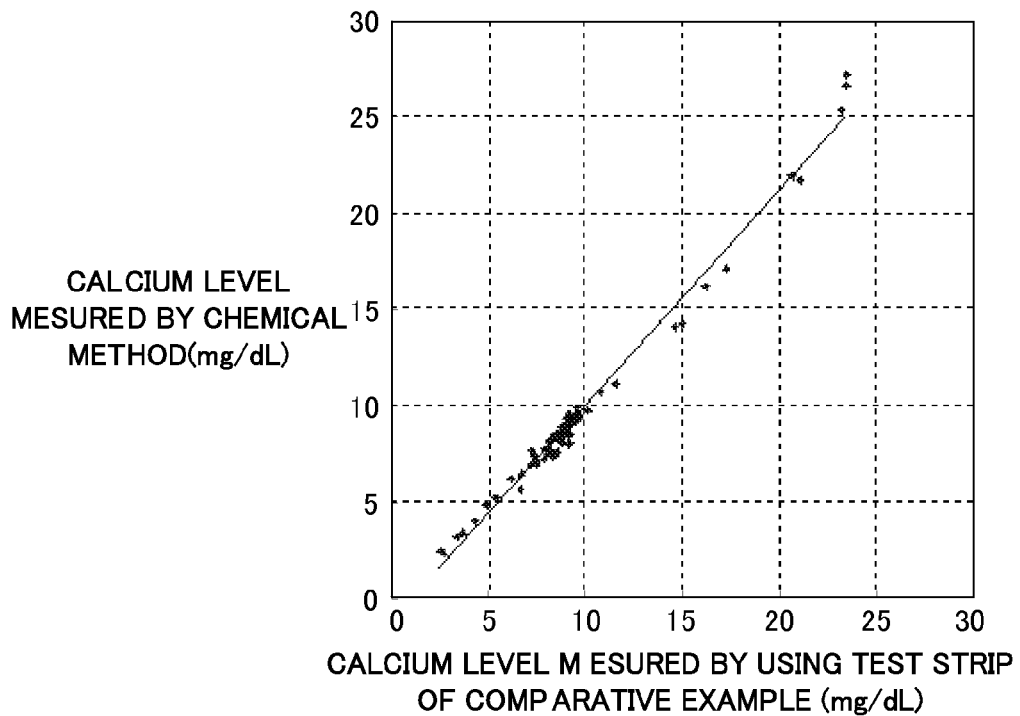
FIG. 4B is a plot of the calcium levels measured by using a dry test strip for measuring calcium of a comparative example of the invention against the calcium levels measured by an enzymatic method.

To compare the accuracy of dry test strips for measuring calcium, the dry test strips of the example and the comparative example were used to measure the level of the calcium in serum specimens of 80 persons of which calcium level had been measured in advance by a chemical method. CALCIUME-HA TEST WAKO (from Wako Pure Chemical Industries) was used to measure the calcium level by the chemical method. FIGS. 4A and 4B show a plot of the calcium levels measured by the chemical method against the calcium levels measured by using one of the dry test strips for measuring calcium. FIGS. 5A and 5B show the difference of a calcium level measured by using one of the dry test strips from a calcium level measured by the chemical method where the level measured by the chemical method is set to 100%. The calcium levels measured by using the dry test strip of the example had a higher correlation coefficient with the calcium levels measured by the chemical method than the calcium levels measured by using the dry test strip of the comparative example. The difference values of a calcium level measured by using the dry test strip of the comparative example from a calcium level measured by the chemical method were widely distributed in the range of from −20% to +15%, and the distribution is biased. On the other hand, when the dry test strip for measuring calcium of the example was used, the difference values were uniformly distributed in the relatively narrow range of from −10% to +10%.

Having described and illustrated the principles of this application by reference to preferred embodiments, it should be apparent that the preferred embodiments may be modified in arrangement and detail without departing from the principles disclosed herein and that it is intended that the application be construed as including all such modifications and variations insofar as they come within the spirit and scope of the subject matter disclosed herein.

What is claimed is:

1. A dry test strip for measuring calcium which is comprising:
   o-cresolphthalene complexone,
   a magnesium selective masking agent, and
   a pH buffer for adjusting the pH of the environment for reaction of the o-cresolphthalene complexone with calcium to 10.0-11.0,
   wherein the pH buffer is at least one selected from the group consisting of N-methyl-D-glucamine alone and N-methyl-D-glucamine in combination with N-cyclohexyl-3-aminopropanesulfonic acid.

2. The dry test strip for measuring calcium according to claim 1, wherein the pH buffer is a 9:1 mixture of N-cyclohexyl-3-aminopropanesulfonic acid and N-methyl-D-glucamine.

3. The dry test strip for measuring calcium according to claim 1, wherein the magnesium selective masking agent is 8-hydroxyquinoline.

4. The dry test strip for measuring calcium according to claim 2, wherein the magnesium selective masking agent is 8-hydroxyquinoline.

5. The dry test strip for measuring calcium according to claim 1, said dry test strip further comprising a surfactant.

6. The dry test strip for measuring calcium according to claim 2, said dry test strip further comprising a surfactant.

7. The dry test strip for measuring calcium according to claim 3, said dry test strip further comprising a surfactant.

8. The dry test strip for measuring calcium according to claim 5, wherein the surfactant is p-t-octyl phenol polyoxyethylene.

9. The dry test strip for measuring calcium according to claim 6, wherein the surfactant is p-t-octyl phenol polyoxyethylene.

10. The dry test strip for measuring calcium according to claim 7, wherein the surfactant is p-t-octyl phenol polyoxyethylene.

11. The dry test strip for measuring calcium according to claim 1 further comprising:
    a support,
    a reagent layer provided on the support, and
    a reagent holding layer provided on the reagent layer, wherein the o-cresolphthalene complexone and the magnesium selective masking agent are contained in the reagent layer, and the pH buffer is contained in the reagent holding layer.

12. The dry test strip for measuring calcium according to claim 2 further comprising:
   a support,
   a reagent layer provided on the support, and
   a reagent holding layer provided on the reagent layer,
   wherein the o-cresolphthalene complexone and the magnesium selective masking agent are contained in the reagent layer, and the pH buffer is contained in the reagent holding layer.

13. The dry test strip for measuring calcium according to claim 3 further comprising:
   a support,
   a reagent layer provided on the support, and
   a reagent holding layer provided on the reagent layer,
   wherein the o-cresolphthalene complexone and the magnesium selective masking agent are contained in the reagent layer, and the pH buffer is contained in the reagent holding layer.

14. The dry test strip for measuring calcium according to claim 5 further comprising:
   a support,
   a reagent layer provided on the support, and
   a reagent holding layer provided on the reagent layer,
   wherein the o-cresolphthalene complexone and the magnesium selective masking agent are contained in the reagent layer, and the pH buffer is contained in the reagent holding layer.

15. The dry test strip for measuring calcium according to claim 8 further comprising:
   a support,
   a reagent layer provided on the support, and
   a reagent holding layer provided on the reagent layer,
   wherein the o-cresolphthalene complexone and the magnesium selective masking agent are contained in the reagent layer, and the pH buffer is contained in the reagent holding layer.

* * * * *